United States Patent
Lacey et al.

(10) Patent No.: US 12,121,665 B2
(45) Date of Patent: Oct. 22, 2024

(54) SYSTEMS AND METHODS FOR MANAGING MOISTURE FOR MEDICAL DEVICES

(71) Applicant: GE Precision Healthcare LLC, Wauwatosa, WI (US)

(72) Inventors: Joseph J. Lacey, Madison, WI (US); Russell J. Kuzelka, Madison, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 888 days.

(21) Appl. No.: 17/196,117

(22) Filed: Mar. 9, 2021

(65) Prior Publication Data

US 2022/0288341 A1    Sep. 15, 2022

(51) Int. Cl.
*A61M 16/08* (2006.01)
*A61M 16/00* (2006.01)
*A61M 16/20* (2006.01)

(52) U.S. Cl.
CPC .... *A61M 16/0808* (2013.01); *A61M 16/0003* (2014.02); *A61M 16/0891* (2014.02); *A61M 16/20* (2013.01); *A61M 2205/053* (2013.01); *A61M 2205/3389* (2013.01); *A61M 2205/36* (2013.01)

(58) Field of Classification Search
CPC .......... A61M 16/0808; A61M 16/0003; A61M 16/0891; A61M 16/20; A61M 16/10; A61M 16/1095; F22B 1/284
See application file for complete search history.

(56) References Cited

U.S. PATENT DOCUMENTS

| | | | |
|---|---|---|---|
| 3,454,005 A | 7/1969 | Eubanks et al. | |
| 4,558,696 A | 12/1985 | Eiserman et al. | |
| 4,822,533 A * | 4/1989 | Steiner | F24F 6/043 261/104 |
| 5,398,677 A * | 3/1995 | Smith | A61M 16/0808 128/205.27 |

(Continued)

FOREIGN PATENT DOCUMENTS

| | | |
|---|---|---|
| EP | 2514472 A2 | 10/2012 |
| WO | WO-03075992 A1 * | 9/2003 |

OTHER PUBLICATIONS

EP application 22158403.0 filed Feb. 24, 2022—Search Report issued Jul. 27, 2022; 7 pages.

*Primary Examiner* — Margaret M Luarca
(74) *Attorney, Agent, or Firm* — Andrus Intellectual Property Law, LLP

(57) ABSTRACT

A moisture management system for a medical device. A water trap has an inlet, outlet, first reservoir, and drain, the inlet receiving gas from a supply connection and the outlet returning the gas to a patient connection. The water trap removes moisture from the gas flowing from the inlet to the outlet, where the moisture removed is held in the first reservoir. The system further includes an evaporation chamber having an inlet, an exhaust, and a second reservoir. The inlet is fluidly coupled to the drain of the water trap to receive the moisture from the first reservoir. The moisture is subsequently held in the second reservoir. The evaporation chamber is configured such that the moisture evaporates from the second reservoir and exits as vapor via the exhaust. An evaporator increases a rate at which the moisture in the second reservoir evaporates via the exhaust.

20 Claims, 10 Drawing Sheets

(56) References Cited

U.S. PATENT DOCUMENTS

| | | | | |
|---|---|---|---|---|
| 5,855,203 A | * | 1/1999 | Matter | A61M 16/08 128/207.14 |
| 6,523,538 B1 | | 2/2003 | Wikefeldt | |
| 2012/0266888 A1 | | 10/2012 | Dwyer | |
| 2017/0216552 A1 | * | 8/2017 | Goff | A61M 16/16 |
| 2022/0273903 A1 | * | 9/2022 | Bao | A61M 13/003 |

\* cited by examiner

SYSTEMS AND METHODS FOR MANAGING MOISTURE FOR MEDICAL DEVICES

FIELD

The present disclosure generally relates to systems and methods for managing moisture for medical devices, and more particularly to moisture management for medical devices having a supply connection for receiving gas.

BACKGROUND

The present disclosure generally relates to medical devices having connections to external gas supplies, such as anesthesia machines and ventilators, for example. Anesthesia machines are medical devices known in the art used to deliver a mix of gases and anesthetic agents to a patient for the purposes of inducing and maintaining anesthesia. An exemplary anesthesia machine presently known in the art is the Aisys $CS^2$ by GE Healthcare®. Similarly, a ventilator is a medical device that provides mechanical ventilation to move air in and out of the lungs of a patient, which may be used alone or in conjunction with the functions described above when incorporated with an anesthesia machine. An exemplary ventilator presently available in the market is the Carescape R860 Ventilator by GE Healthcare®.

In each case, the medical device is typically connected to an incoming gas supply connection, which in the example of use in a hospital context may include medical-grade oxygen to be delivered to the patient. The oxygen may be mixed with other gases and/or anesthetic agents as needed.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

One embodiment of the present disclosure generally relates to a moisture management system for a medical device having a supply connection for receiving gas and a patient connection for supplying the gas to a patient, The system includes a water trap having an inlet, an outlet, a first reservoir, and a drain, the inlet receiving the gas from the supply connection and the outlet returning the gas to the patient connection, where the water trap is configured to remove moisture from the gas flowing from the inlet to the outlet, and where the moisture removed is held in the first reservoir. The system further includes an evaporation chamber having an inlet, an exhaust, and a second reservoir, where the inlet is fluidly coupled to the drain of the water trap to receive the moisture from the first reservoir, where the moisture is subsequently held in the second reservoir, and where the evaporation chamber is configured such that the moisture evaporates from the second reservoir and exits as vapor via the exhaust. An evaporator increases a rate at which the moisture in the second reservoir evaporates via the exhaust.

In certain embodiments, the evaporator is a fan that blows air across the moisture in the second reservoir to increase the rate of evaporation from the evaporation chamber.

In certain embodiments, the evaporator is a wick positioned to draw the moisture upwardly from the second reservoir to increase the rate of evaporation from the evaporation chamber.

In certain embodiments, the evaporator is a heater positioned in the second reservoir such that the heater warms the moisture therein to increase the rate of evaporation from the evaporation chamber.

In certain embodiments, the heater is a PTC heater.

In certain embodiments, the heater is configured to remain at or below 50° C.

In certain embodiments, the system further includes a first level sensor positioned to detect when the moisture in the first reservoir exceeds a first threshold, and a drain valve fluidly coupled between the drain of the water trap and the inlet of the evaporation chamber to control flow therebetween, where the drain valve is normally closed. The system further includes a control system coupled to the first level sensor and the drain valve, where the control system causes the drain valve to open while the first level sensor detects that the moisture in the first reservoir exceeds the first threshold.

In certain embodiments, the system further includes a bypass valve that bypasses the water trap to fluidly couple the supply connection and the patient connection, where the bypass valve is normally closed, and where the control system further causes the bypass valve to open while the first level sensor detects that the moisture in the first reservoir exceeds the first threshold.

In certain embodiments, the system further includes a first water trap valve fluidly coupled between the supply connection and one of the inlet and the outlet of the water trap to control flow therebetween, where the first water trap valve is normally open, and where the control system further causes the first water trap valve to close while the first level sensor detects that the moisture in the first reservoir exceeds the first threshold.

In certain embodiments, the first water trap valve is fluidly coupled between the supply connection and the inlet of the water trap, further including a second water trap valve fluidly coupled between the outlet of the water trap and the patient connection to control flow therebetween, where the second water trap valve is normally open, and wherein the control system further causes the second water trap valve to close while the first level sensor detects that the moisture in the first reservoir exceeds the first threshold.

In certain embodiments, the evaporator is a powered device, further including a second level sensor positioned to detect when the moisture in the second reservoir exceeds a second threshold, where the control system increases the power to the evaporator while the second level sensor detects that the moisture in the second reservoir exceeds the second threshold.

In certain embodiments, the system further includes a second level sensor positioned to detect when the moisture in the second reservoir exceeds a second threshold, and also a control system coupled to the second level sensor and the evaporator, where the evaporator is a powered device, and where the control system increases the power to the evaporator while the second level sensor detects that the moisture in the second reservoir exceeds the second threshold.

In certain embodiments, a UV light is positioned to irradiate the moisture within at least one of the first reservoir and the second reservoir.

In certain embodiments, at least one of the first and second reservoirs is configured to be antibacterial.

In certain embodiments, the supply connection supplies the gas to the patient from an anesthesia machine and the patient connection receives the gas from the patient back to the anesthesia machine.

Another embodiment generally relates to a method for managing moisture for a medical device having a supply connection for receiving gas and a patient connection for supplying the gas to a patient. The method includes fluidly coupling a water trap to the primary conduct, the water trap having an inlet, an outlet, a first reservoir, and a drain, the inlet receiving the gas from the supply connection and the outlet returning the gas to the patient connection, where the water trap is configured to remove moisture from the gas flowing from the inlet to the outlet, and where the moisture removed is held in the first reservoir. The method includes fluidly coupling an evaporation chamber to the drain of the water trap, the evaporation chamber having an inlet, an exhaust, and a second reservoir, where the inlet is fluidly coupled to the drain of the water trap to receive the moisture from the first reservoir, where the moisture is subsequently held in the second reservoir, and where the evaporation chamber is configured such that the moisture evaporates from the second reservoir and exits as vapor via the exhaust. The method further includes positioning an evaporator in proximity to the second reservoir such that the evaporator acts on the moisture within the second reservoir to increase a rate at which the moisture evaporates therefrom via the exhaust.

In certain embodiments, the method further includes positioning a first level sensor to detect when the moisture in the first reservoir exceeds a first threshold, fluidly coupling a drain valve between the drain of the water trap and the inlet of the evaporation chamber to control flow therebetween, where the drain valve is normally closed, and coupling a control system to the first level sensor and the drain valve and configuring the control system to cause the drain valve to open while the first level sensor detects that the moisture in the first reservoir exceeds the first threshold.

In certain embodiments, the method further includes fluidly coupling a bypass valve that bypasses the water trap to fluidly couple the supply connection and the patient connection, where the bypass valve is normally closed, fluidly coupling a first water trap valve between the supply connection and one of the inlet and the outlet of the water trap to control flow therebetween, wherein the first water trap valve is normally open, and configuring the control system to further cause the bypass valve to open and the first water trap valve to close while the first level sensor detects that the moisture in the first reservoir exceeds the first threshold.

In certain embodiments, the evaporator is a powered device, further comprising positioning a second level sensor to detect when the moisture in the second reservoir exceeds a second threshold, and further comprising configuring the control system to increase the power to the evaporator while the second level sensor detects that the moisture in the second reservoir exceeds the second threshold.

Another embodiment generally relates to a moisture management system for a medical device having a supply connection for receiving gas and a patient connection for supplying the gas to a patient. The system includes a water trap having an inlet, an outlet, a first reservoir, and a drain, the inlet being coupled via a first water trap valve to the supply connection for receiving the gas therefrom, the outlet being coupled via a second water trap valve to the patient connection for supplying the gas thereto, where the first and second water trap valves are normally open, where the water trap is configured to remove moisture from the gas flowing from the inlet to the outlet, and where the moisture removed is held in the first reservoir. The system includes an evaporation chamber having an inlet, an exhaust, and a second reservoir, where the inlet is fluidly coupled via a drain valve to the drain of the water trap to receive the moisture from the first reservoir, where the drain valve is normally closed, where the moisture is subsequently held in the second reservoir, and where the evaporation chamber is configured such that the moisture evaporates from the second reservoir and exits as vapor via the exhaust. A bypass valve bypasses the water trap to fluidly couple the supply connection and the patient connection, where the bypass valve is normally closed. First and second level sensors are positioned to detect when the moisture in the first and second reservoirs exceeds first and second thresholds, respectively. A fan blows air across the moisture in the second reservoir to increase a rate of evaporation of the moisture from the evaporation chamber. A heater is positioned in the second reservoir such that the heater warms the moisture therein to increase the rate of evaporation from the evaporation chamber. A control system is coupled to the first and second level sensors, the bypass valve, the first and second water trap valves, and the drain valve, where the control system causes the bypass valve to open, the first and second water trap valves to close, and the drain valve to open while the first level sensor detects that the moisture in the first reservoir exceeds the first threshold, and where the control system increases the power to the evaporator while the second level sensor detects that the moisture in the second reservoir exceeds the second threshold.

Various other features, objects and advantages of the disclosure will be made apparent from the following description taken together with the drawings.

BRIEF DESCRIPTION OF THE DRAWINGS

The present disclosure is described with reference to the following drawings.

DETAILED DISCLOSURE

The present disclosure generally relates to systems and methods for managing moisture in medical devices. Through experimentation and development, the inventors have recognized problems with respect to moisture management for medical devices presently known in the art, including but not limited to medical device having a supply connection connected to a gas supply that subsequently supply a gas mixture to a patient. Exemplary gases include oxygen, nitrogen, anesthetic agents, other atmospheric gases, and/or other mixtures thereof as presently known in the art. In particular, the inventors have recognized problems with moisture management for anesthesia devices and ventilators, which in a clinical setting are connected at their respective supply connections to wall gas at a hospital or clinic (providing oxygen or other gases), whereby the patient is then connected via hoses to a patient connection to receive a desired anesthetic mix of gases, ventilation support, or both.

The inventors have recognized that the incoming gas provided at the supply connection often introduces moisture into the medical device, which may be condensed water, oil from various compressors or facility equipment, or other contaminants in addition to the intended gas being supplied. This moisture can cause damage to many different components within the medical device, including from an electrical, mechanical, and/or chemical basis, for example. This moisture also introduces the opportunity for contamination in terms of pathogenic growth inside the medical device, which can then be transferred to the patient.

The inventors have recognized that a similar phenomenon occurs at the patient connector side of the medical device, whereby moisture is introduced into the medical device by virtue of the patient being connected to the patient connection via hoses. For example, moisture is introduced into the medical device via condensation of the patient's warm exhalation gases. As previously discussed, this can cause damage to the internal components of the medical device, and/or may introduce pathogens into the medical device. Unintended moisture also causes problems with seals becoming dirty, which over time impacts the performance thereof.

Certain medical devices presently known in the art provide water traps in an effort to collect this unintended moisture. This may include moisture entering the system from the supply connection, as well as moisture introduced from the patient. However, as is discussed further below, the inventors have found these presently known system to be woefully inadequate in preventing the damage and pathogenic risks described above, with most systems providing no preventative measure at all.

Figure 1:
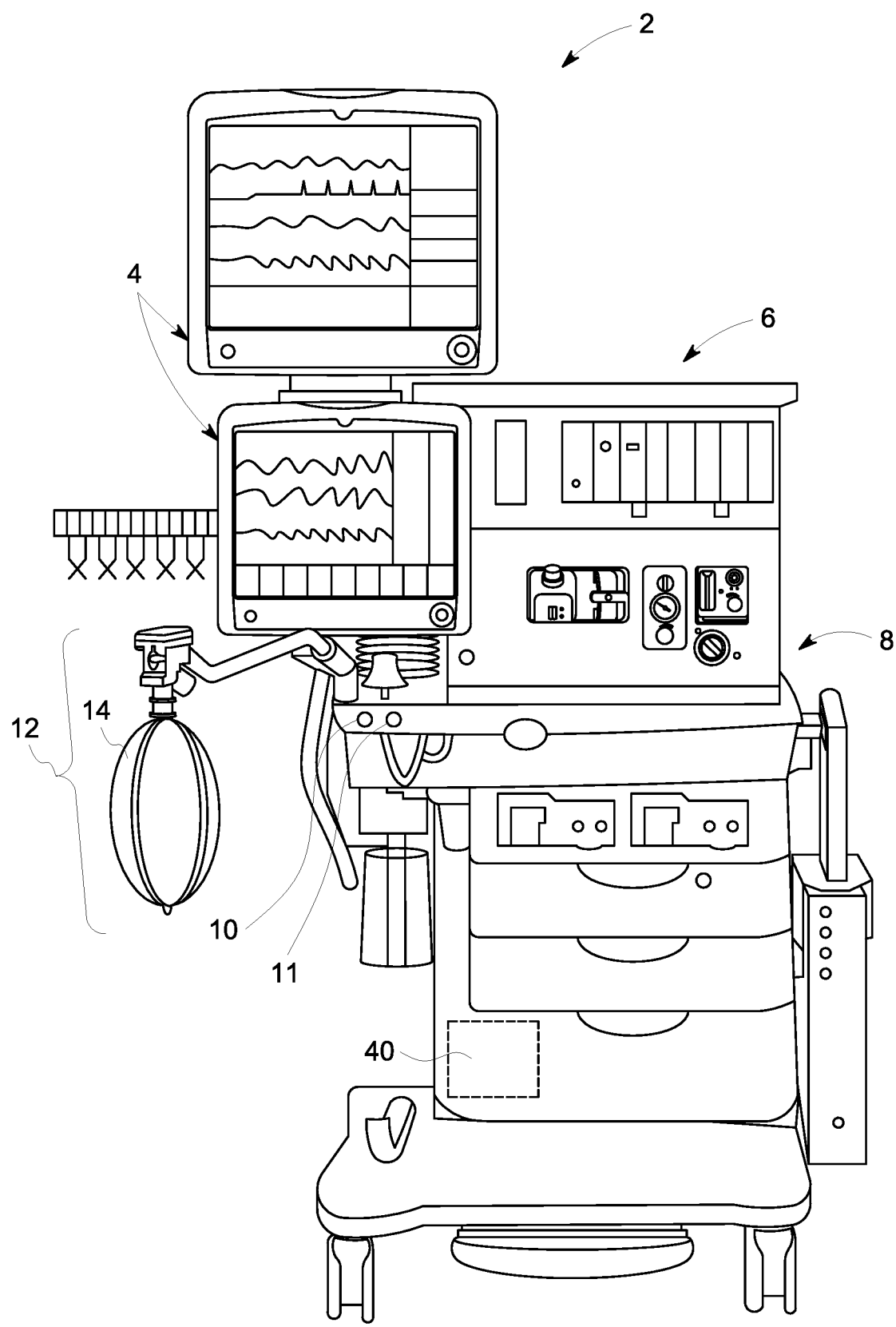
FIG. 1 is a front view of a medical device incorporating a moisture management system according to the present disclosure.

FIG. 1 depicts an exemplary medical device 2 incorporating a moisture management system 40 according to the present disclosure. Other than the addition of the moisture management system presently disclosed, the medical device 2 may be similar to the Aisys CS² anesthesia delivery system by GE Healthcare®. The medical device 2 is controlled via user interface devices 4 to operate the main hardware 6 in a manner known in the art. Incoming gas is supplied to the medical device 2 via a supply connection 8, which may receive oxygen from the wall gas of a hospital, for example.

Figure 2:
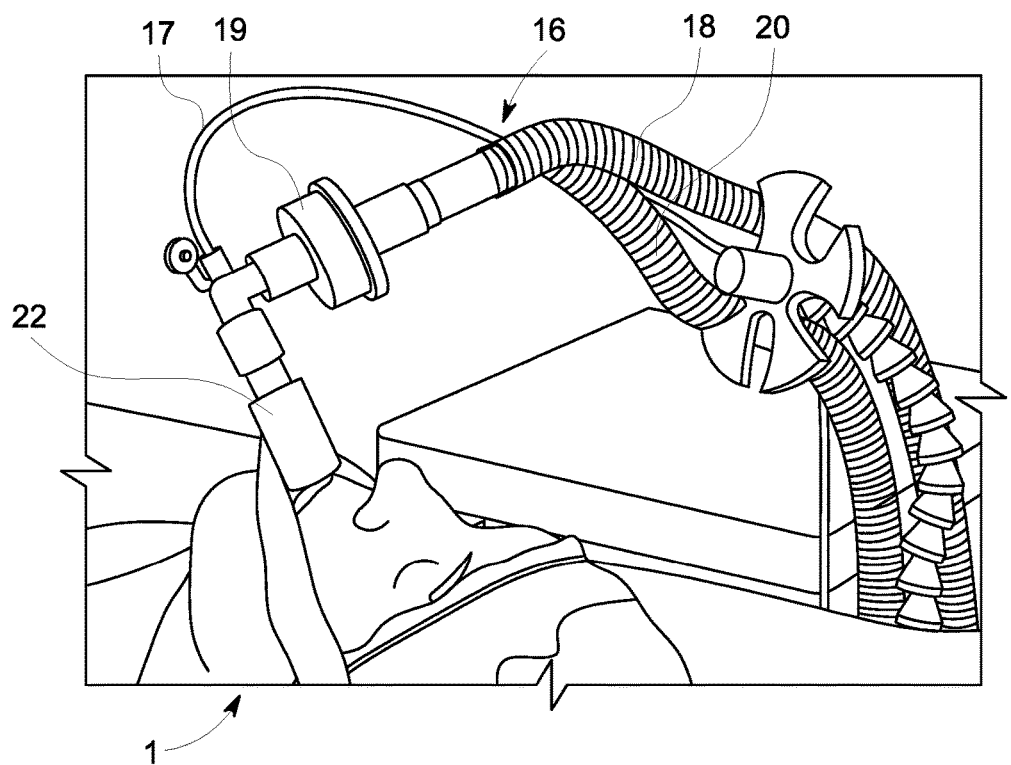
FIG. 2 is a top perspective view of a patient presently receiving a gas mixture from a medical device such as that shown in FIG. 1.

The medical device 2 includes a breathing system 12, which in certain examples includes a manual breathing bag 14. The breathing system 12 provides a flow of gas to the patient via a patient connection 10. As also shown in FIG. 2, the patient connection 10 provides gas to the patient via a patient hose 16, which in the present example has an inhalation side 18 coupled to the patient connection 10 for delivering the gas to the patient 1, as well as an exhalation side 20 for returning gas from the patient 1 back to the medical device 2, particularly to a return connection 11 (FIG. 1). The patient hose 16 of FIG. 2 is connected to the patient 1 at a distal end, presently shown as connecting to an intubation tube 22, but may otherwise be a patient mask, for example.

In certain examples, as shown in FIG. 2, an auxiliary line 17 is provided an alternative route for communicating gas from the patient 1 to the medical device 2, as discussed further below. The depiction of FIG. 2 also includes a moisture trap 19 that in some examples is connected between the patient 1 and the medical device 2 as a means for preventing moisture from transferring therebetween.

Figure 3:
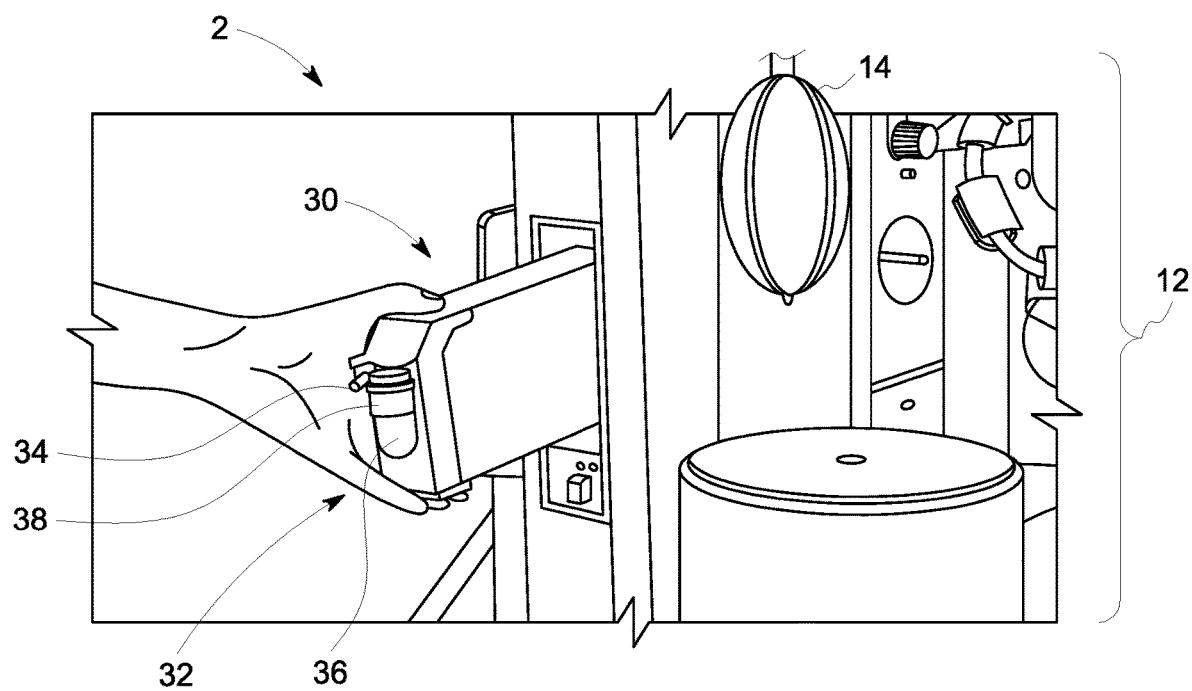
FIG. 3 is a perspective side view of a medical device similar to that shown in FIG. 1, but incorporating a cartridge system including a water trap system presently known in the art.
Figure 4A:
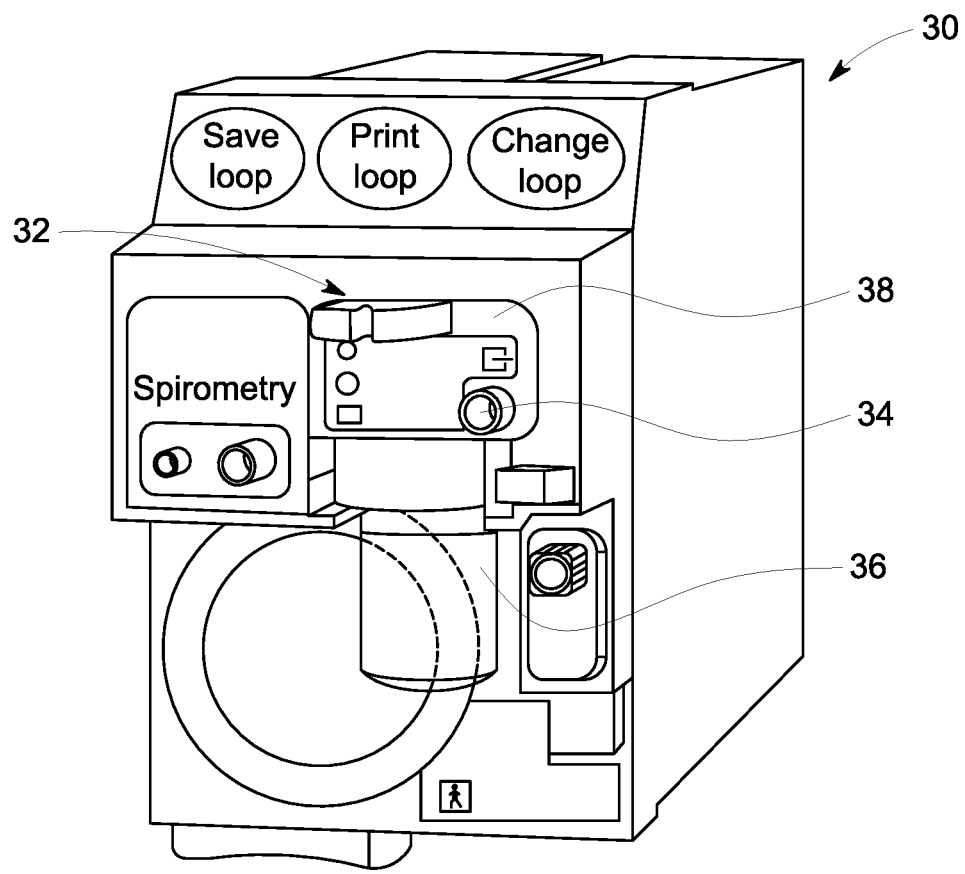
FIG. 4A is a front isometric view of another cartridge system with a water trap system as presently known in the art.
Figure 4B:
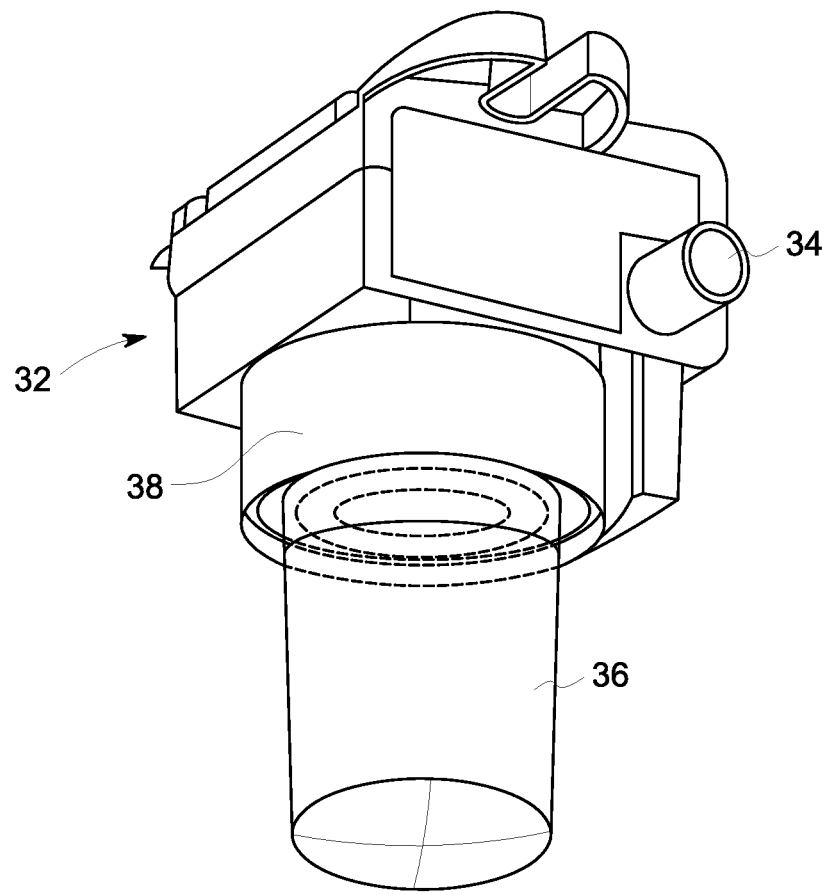
FIG. 4B is a front perspective view of the water trap system of FIG. 4A removed from the cartridge system.

FIGS. 3 and 4A-4B depict exemplary systems presently known in the art for preventing moisture from entering the medical device 2 from the patient 1. FIG. 3 depicts a cartridge system 30 insertable into the side of a medical device 2, similar to that shown in FIG. 1, which includes a water trap system 32. A similar cartridge system 30 is also in FIG. 4A, with its water trap system 32 removed therefrom in FIG. 4B. The cartridge systems 30 are typically add-on items that provided additional functionality to the medical device 2, such as additional gas analysis. In each example of cartridge system 30 shown, the water trap system 32 includes an inlet 34 that receives gas from the patient, for example via the auxiliary line 17 shown in FIG. 2. The water trap system 32 further includes a reservoir 36 that in the present example is threadedly removable from a base 38. In the examples shown, a zig-zag pattern is defined within the water trap system 32 (as known in the art) such that moisture introduced via the inlet 34 condenses and is directed to the reservoir 36. The reservoir 36 must then be periodically, manually dumped out by a clinician as it fills to prevent an overflow in which the moisture damages the cartridge system 30.

A similar zig-zag pattern may also be defined within the medical device 2 itself (i.e., to protect the medical device 2 in a similar manner as the cartridge system 30), typically just downstream of the supply connection 8. For medical devices presently known in the art that include such a zig-zag pattern, the condensed moisture is either lead to a tray within the inside of the medical device, or onto the floor of the room. These solutions either lead to a puddle on the floor, or another need for manual draining of the tray before overflowing, leading to the problems discussed above. Namely, manual intervention to drain various trays or traps is problematic in that a failure to do such manual draining results in moisture entering the medical device and/or breathing circuits, damaging equipment and/or introducing pathogens for the patient. Similarly, the drain system creates risks when overflowing, leading to water on the floor, for example.

Accordingly, the systems and methods presently disclosed solve the unmet needs of not only provide for collecting moisture from incoming supply lines and/or as introduced from the patient, but also eliminate the requirement for the manually draining this collected moisture. As is discussed further below, the systems and methods presently disclosed generally provide for collecting this moisture from the various sources, then vaporizing it to be harmlessly returned to the room automatically and as needed.

Figure 5:
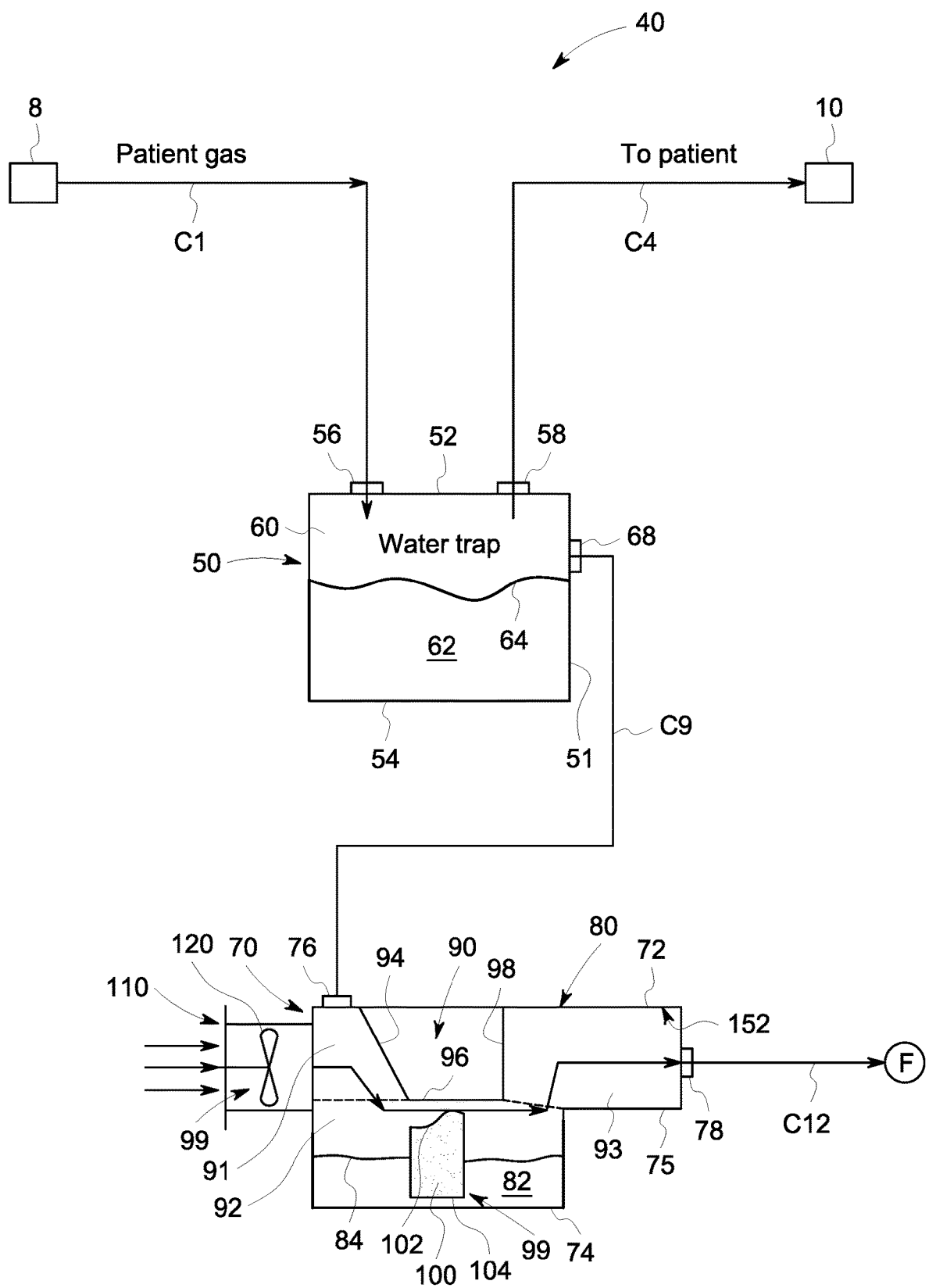
FIG. 5 is an exemplary schematic of a moisture management system according to the present disclosure, such as that incorporated within the medical device shown in FIG. 1.

FIG. 5 depicts a first moisture management system 40 for a medical device 2 according to the present disclosure. A supply connection 8 is configured for receiving gas within the medical device 2, for example connected to the wall gas of a hospital room. Likewise, a patient connection 10 is provided for supplying gas from the medical device 2 to the patient in the manner previously discussed. As such, the remaining elements of the moisture management system 40 presently shown may be contained within the medical device 2 so as to not in typical use be viewable by the physicians or patient. However, it should be recognized that the present disclosure also contemplates moisture management systems 40 that are in whole or part external to the medical device 2 for accessibility, ease of retrofitting into existing medical devices, and/or the like.

The moisture management system 40 includes a water trap 50 that extends between a top 52 and bottom 54. In the example shown, an inlet 56 and outlet 58 for communicating gas to and from the water trap 50, respectively, are each provided within the top 52 of the water trap 50. However, it should be recognized that the positioning of the inlet 56 and/or outlet 58 may be in alternate positions, for example on one of the sides of the water trap 50 between the top 52 and bottom 54. Conduits C1-C12 (see FIG. 6) connect the inlet 56 and outlet 58 to the supply connection 8 and patient connection 10, which may be made of flexible tubing, rigid plastic, metal, or other materials known in the art for communicating gases and liquids (being configured to withstand all types of gases and anesthetic agents to flow therethrough).

Figure 6:
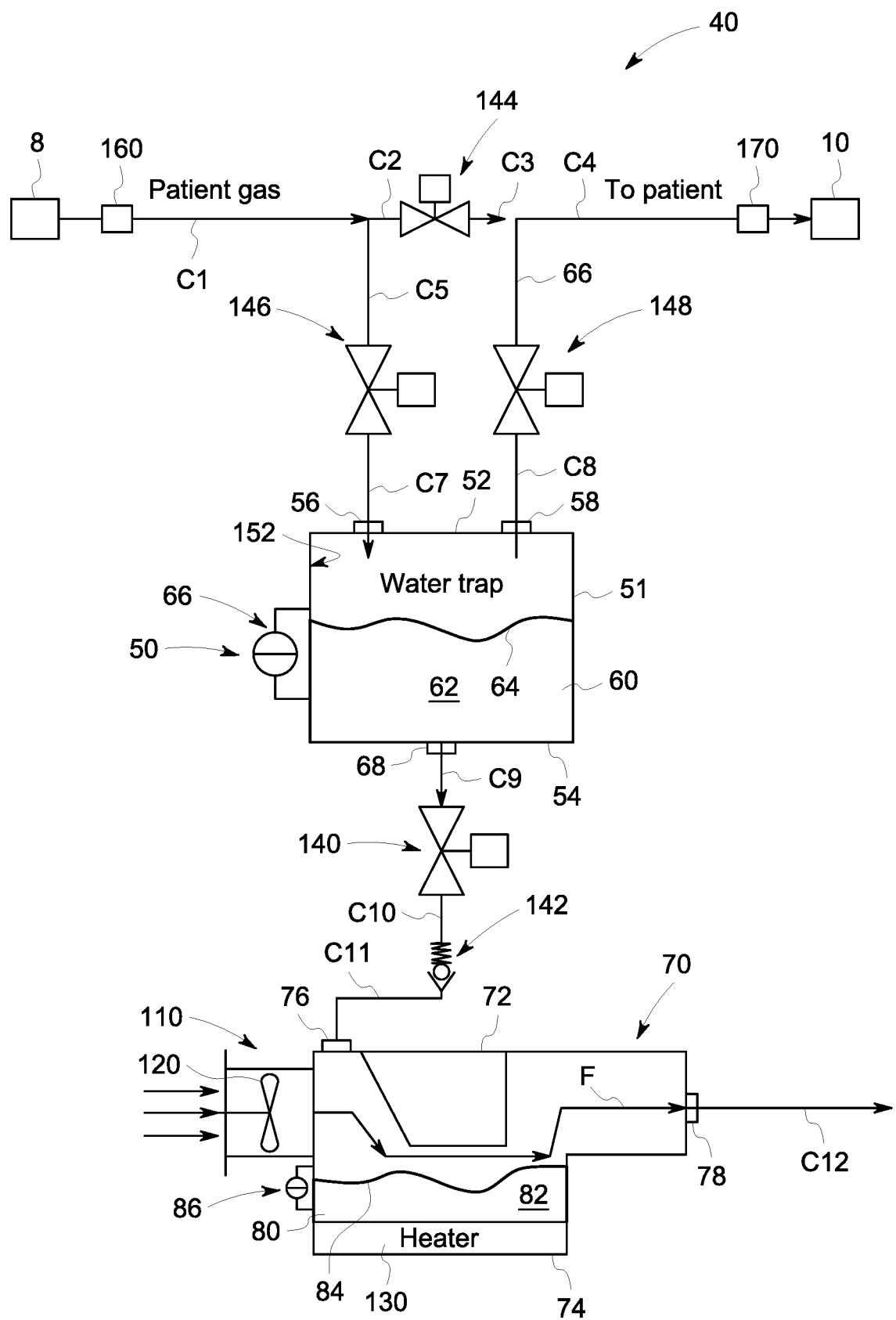
FIG. 6 is another exemplary schematic of a moisture management system according to the present disclosure, such as that incorporated within the medical device shown in FIG. 1.

With continued reference to FIG. 5, the water trap 50 includes a first reservoir 60 by which moisture 62 is condensed from the gas flowing between the inlet 56 and the outlet 58, for example via methods known in the art, including zig-zag patterns therein. Unlike systems presently known in the art, this first reservoir 60 will be automatically drained via a drain 68 as needed, which is discussed further below. In this example, the drain 68 is provided in the side 51 of the water trap 50 just above a fill level 64 in which it would be desirable to begin draining the moisture 62 within the water trap 50. However, it should be recognized that the present disclosure contemplates other locations for positioning the drain 68 (e.g., as shown in FIG. 6). In this manner, the water trap 50 is configured to remove the moisture from the gas flowing from the inlet 56 to the outlet 58, wherein this moisture 62 is retained within the first reservoir 60, presently shown at a fill level 64.

The moisture management system 40 further includes an evaporation chamber 70 that extends between a top 72 and bottom 74. An inlet 76 is provided in the top 72 of the evaporation chamber 70, which is fluidly coupled to the drain 68 of the first reservoir 60 in the water trap 50 (e.g., using the conduit C9 as discussed above). The evaporation chamber 70 also includes an exhaust 78. A second reservoir 80 is fluidly coupled to both the inlet 76 and the exhaust 78. As such, the moisture received from the water trap 50 via the inlet 76 of the evaporation chamber 70 is retained within the second reservoir 80, shown as the moisture 82 having a fill level 84.

With continued reference to FIG. 5, the evaporation chamber 70 is configured such that the moisture 82 retained within the second reservoir 80 evaporates from the second reservoir 80 (for example into the room in which the medical device 2 is positioned) to exit as vapor via the exhaust 78. This evaporation process is expedited by the inclusion of one or more evaporators 99 that act upon the moisture 82 within the second reservoir 80 to increase the rate at which this moisture 82 evaporates via the exhaust 78 relative to a system in which no evaporator 99 is present.

In the example shown in FIG. 5, two evaporators 99 are provided. A first evaporator 99 is a wick 100 that extends between a top 102 and a bottom 104. With the fill level 84 of the moisture 82 as presently shown, the bottom 104 of the wick 100 is fully submerged within the moisture 82, whereas the top 102 extends at least in part above the fill level 84 such that the wick 100 may draw the moisture 82 upwardly to encourage evaporation from the second reservoir 80. The wick 100 may be made of solid or interwoven materials known in the art to soak up liquids, for example plastics with tuned porosity (e.g., Delrin), cotton fiber, wool, sintered metal (e.g., aluminum, stainless steel), ceramic, nylon, or acrylic, to name a few. In this example, a second evaporator 99 is also provided, which here is a power device 110, and specifically a fan 120. As shown, the fan 120 directs air across the surface of the moisture 82 within the second reservoir 80, encouraging evaporation therefrom, as well as across the wick 100 to improve the performance of the wick 100 in evaporating moisture therefrom. In this manner, the fan 120 expedites the rate at which the moisture 82 is evaporated from the second reservoir 80 via the exhaust 78. In the example shown, the fan 120 may draw room air, for example from the back of the medical device 2, in one side of the evaporation chamber 70, with the exhaust 78 being positioned on an opposite side of the second reservoir 80 to optimize the air flow therebetween. The fan 120 may be an AC or DC electric fan as presently known in the art.

In certain embodiments, an air funnel 90 is also provided within the evaporation chamber 70 to assist in concentrating the flow of air provided by the fan 120 through the exhaust 78. The air funnel 90 is comprised of a first wall 94 extending downwardly from the top 72 of the evaporation chamber 70, a second wall 96 substantially parallel to the top 72, and a third wall 97 connecting to the second wall 96 and also the top 72. In the configuration of FIG. 5, the air funnel 90 effectively divides the second reservoir 80 into a first chamber 91 before the air funnel 90, a second chamber 93 below the air funnel 90, and a third chamber 95 downstream of the air funnel 90. This configuration is intended to direct the flow of air from the fan 120 downwardly towards the moisture 82 retained in the second reservoir 80, thereby increasing the flow across the surface and thus increasing the effectiveness in expediting evaporation. In the example shown, the first wall 94 in particular of the air funnel 90 directs this air movement towards the wick 100, also enhancing the effectiveness thereof.

In the configuration of FIG. 5, after the concentrated airflow within the second chamber 93 of the second reservoir 80, the third chamber 95 then opens up again to the full height of the evaporation chamber 70 up to the top 72 to encourage evaporation of the moisture 82 from the second reservoir 80 to exit. The fan 120 again assists in this movement of the air now containing the evaporated moisture, which exits via the exhaust 78 into the room.

As shown in FIG. 6, other examples of evaporators 99 may also or alternatively be incorporated, such as a heater 130 provided as an additional power device 110. In this example, the moisture 82 within the second reservoir 80 is heated by the heater 130 to again encourage evaporation therefrom. The heater 130 may work alone or in conjunction with other evaporators 99, in this example with a fan 120. In certain embodiments, the heater 130 is a PTC heater configured to heat the moisture 82 to a pre-configured temperature without the need for a dedicated control system. In certain embodiments, the PTC heater is pre-configured to not exceed 50° C. The present inventors have recognized that by configuring the PTC heater in this manner is advantageous in eliminating a risk of burning a user or patient if accidental contact were made with the heater 130, and/or moisture 82 contained within the second reservoir 80. The inventors have recognized that this is further advantageous in avoiding costly shielding or mitigating features to prevent this accidental burning, offering a cost-saving measure and simplified design for retrofitting medical devices presently known in the art. However, it should be recognized that other temperatures of the heater 130 are also contemplated by the present disclosure, including those in which the heater 130 is configured to boil the moisture 82 to thereby create steam for evaporation.

The embodiment of FIG. 6 also depicts various other features distinct from the moisture management system 40 shown in FIG. 5. Among other things, the moisture management system 40 of FIG. 6 includes a series of valves and sensors that provide further safeguards and intelligence to the draining and evaporation process. It should be recognized that further hybrids are anticipated between the embodiments of FIGS. 5 and 6, for example including differing numbers of valves and in differing locations, as well as differing sensors, for example. In the embodiment shown, a bypass valve 144 is coupled between the supply connection 8 and patient connection 10. The bypass valve 144 is normally closed, but may be actuated to fluidly couple the supply connection 8 and the patient connection 10 to thus bypass the water trap 50. Likewise, a first water trap valve 146 and second water trap valve 148 are provided between the supply connection 8 and inlet 56 of the water trap 50, and between the outlet 58 of the water trap 50 and the patient connection 10, respectively. In the embodiment shown, the first and second water trap valves 146, 148 are normally open, providing for the water trap 50 to withdraw moisture from the gas being exchanged between the supply connection 8 and patient connection 10 in a manner known in the art. It should be recognized that this path is most effective when the bypass valve 144 is closed, whereby the bypass valve 144 would otherwise provide a path of least resistance directly between the supply connection 8 and patient connection 10.

The embodiment of FIG. 6 further includes a drain valve 140, as well as a one-way valve 142, which together provide a fluid connection between the drain 68 of the water trap 50 and the inlet 76 of the evaporation chamber 70. In the embodiment shown, the drain valve 140 is normally closed, but operable to open and thereby drain the water trap 50 under circumstances such as described below.

FIG. 6 further depicts a moisture management system 40 that includes a first sensor 66 configured to detect the fill level 64 of moisture 62 within the first reservoir 60 of the water trap 50, as well as a second level sensor 86 that detects the fill level 84 of moisture 82 within the second reservoir 80 of the evaporation chamber 70. It will be recognized that the first level sensor 66 and/or second level sensor 86 may be configured to measure the levels within the first reservoir 60 and second reservoir 80 on a continuous basis, or may be configured as a go, no-go detector, such as a float within a sump pump or toilet tank.

Figure 7:
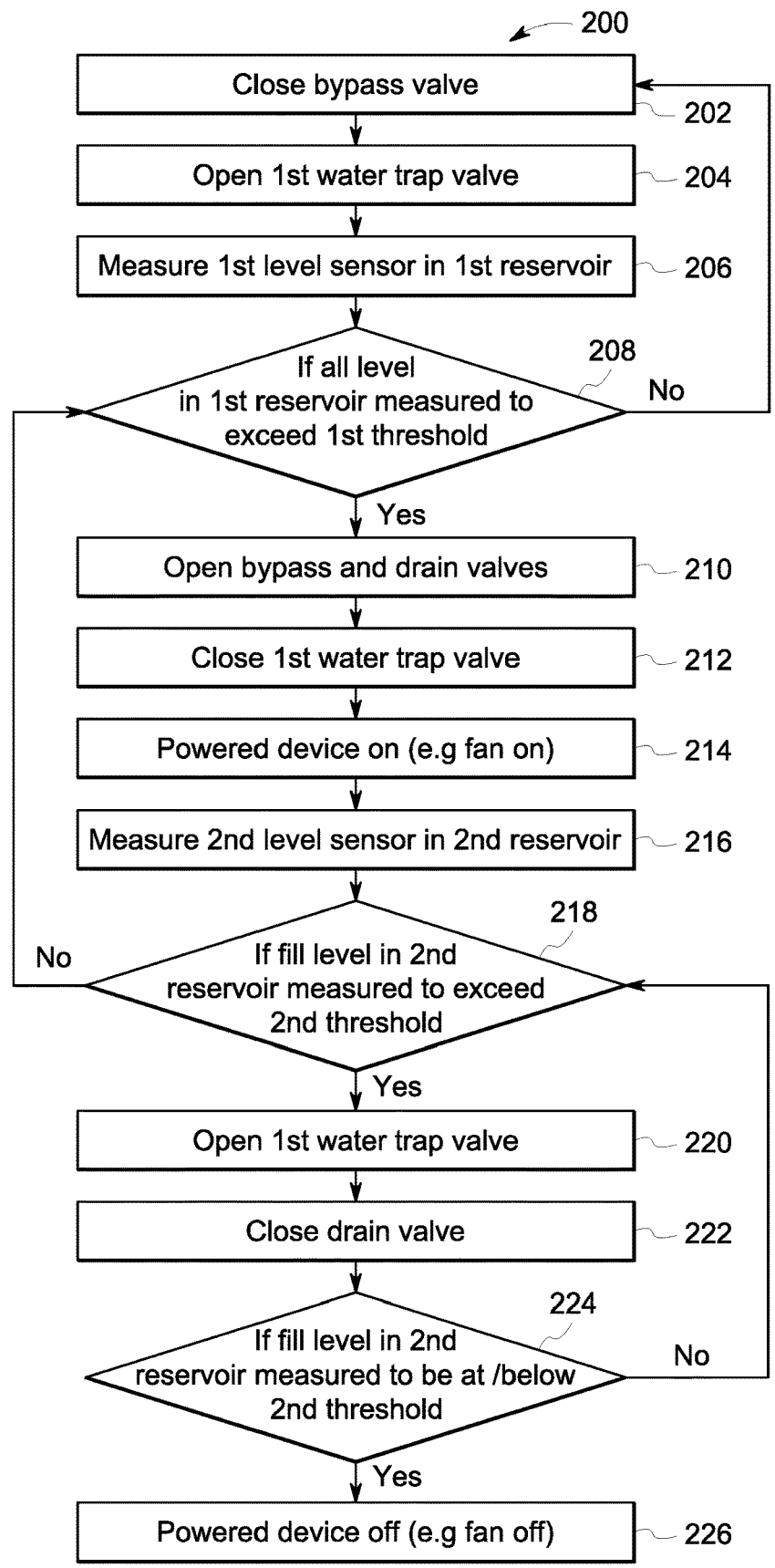
FIG. 7 is a flowchart for an exemplary method for managing moisture for a medical device according to the present disclosure.

An exemplary method 200 for operating the configuration of FIG. 6 is provided in FIG. 7. In the method 200 shown, step 202 provides for closing the bypass valve 144, which as previously stated is configured as a normally closed valve of a type presently known in the art. Similarly, step 204 provides for opening the first water trap valve 146, which in certain embodiments such as that shown in FIG. 6 also provides for opening a second water trap valve 148, which as previously discussed are normally open and of a type of valve presently known in the art. Step 206 then provides for measuring with the first level sensor a fill level in the first reservoir. If it is then determined in step 208 that the fill level in the first reservoir is measured to exceed a first threshold, the process continues with steps 210 through 214, whereas in the alternate the process returns with step 202.

When the fill level does exceed a first threshold as determined in step 208, step 210 provides for opening the bypass and drain valves 144, 140, thereby enabling the moisture 62 within the first reservoir 60 of the water trap 50 to drain via the drain 68 and thereby enter the evaporation chamber 70. At the same time, step 212 provides for closing the first water trap valve 146 (and in the example of FIG. 6 the second water trap valve 149) to prevent any communication between the water trap 50 and the supply connection 8 and/or the patient connection 10 while the draining of the water shaft 50 is in progress. It should be recognized that this closing of the first and second water trap valves 146, 148 is not necessary in all embodiments; however, the inventors have found it advantageous in certain configurations to limit the movement of moisture 62 from the water trap 50 other than in the intended direction, namely only permitting this moisture 62 to exit the water trap 50 via the drain 68.

In embodiments in which a powered device 110 is provided, this powered device (e.g., a fan 120 and heater 130) are turned on in step 214. It should be recognized that in certain embodiments, one or more of the powered devices 110 may remain operational at all times, and/or in these cases step 214 may provide for one or more of the powered devices 110 operating at a different power level. For example, the powered devices 110 may be controlled to increase a flow rate of the fan 120 and/or increase the heat produced by the heater 130 as the moisture is introduced from the water trap 50 to the evaporation chamber 70, and/or as a function of the fill level 84 as discussed below, for example.

Step 216 then provides for measuring with a second level sensor 86 the fill level 84 within the second reservoir 80 for the evaporation chamber 70. If it is determined in step 218 that the fill level 84 in the second reservoir 80 exceeds a second threshold, the process continues from steps 220 through 226. In the alternate, if the fill level is not determined to exceed the second threshold in step 218, the process returns to step 208.

When the fill level 84 in the second reservoir 80 exceeds the second threshold as determined in step 218, step 220 provides for opening the first water trap valve 146 (and in the embodiment of FIG. 6 also the second water trap valve 148), and step 222 provides for closing the drain valve 140.

The closure of the drain valve 140 is to prevent additional moisture 62 from entering the evaporation chamber 70 until the fluid level 84 within the second reservoir 80 once again returns to a fill level 84 below the second threshold. In other words, the drain valve 140 prevents the evaporation chamber 70 from being overfilled. The closure of the drain valve 140 also prevents evaporation of the moisture 82 from the evaporation chamber 70 back towards the water trap 50, particularly in embodiments that do not incorporate a one-way valve 142 as shown in FIG. 6.

Once it is determined in step 224 that the fill level in the second reservoir 80 is at or below the second threshold, step 226 provides for turning off the power devices 110, or as previously described intentionally modifying one or more of the powered devices 110 to operate at a reduced power level.

It will be recognized that the one or more powered devices 110 need not operate at simply a two-step process (for example on versus off, or low power versus high power), but may also operate at intermediate levels depending on the measurements of the first level sensor 66 and/or second level sensor 86, for example.

In certain embodiments, the moisture management system 40 includes sanitization features for preventing bacterial, viral, fungal, or other deleterious growth or buildup within the system, for example, but not limited to within the water trap 50 and evaporation chamber 70. For example, in the embodiment of FIG. 5, an anti-bacterial coating 152 is applied to the interior of the second reservoir 80 to prevent growth therein. This sanitization may be provided as a coating such as that previously described, and/or through the selection of the materials comprising the elements themselves. In this manner, the moisture management system 40 serves as a failsafe for the medical device 2, both to prevent moisture from reaching undesirable locations, and to prevent pathogenic growth (here providing redundancy via the sanitization and evaporators 99).

Figure 8A:
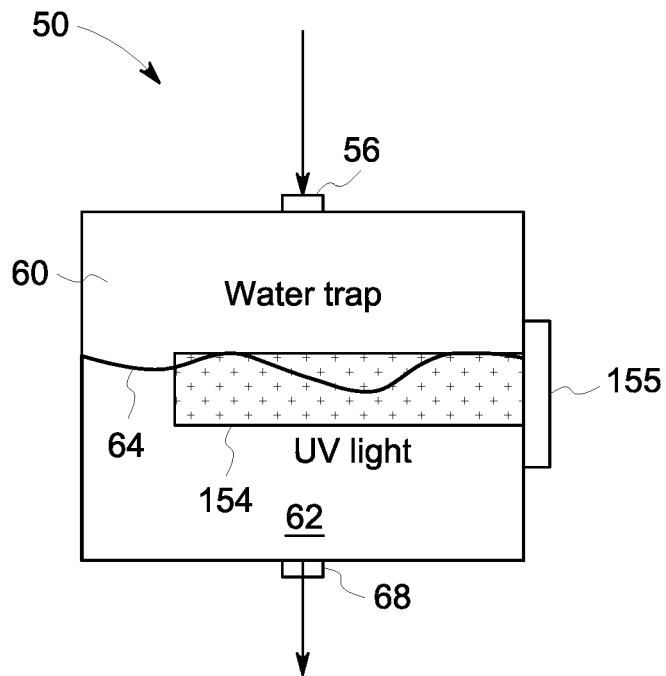
FIGS. 8A and 8B depict side and top views of an alternate embodiment of water trap as may be incorporated within the systems depicted in FIGS. 5 and 6.
Figure 8B:
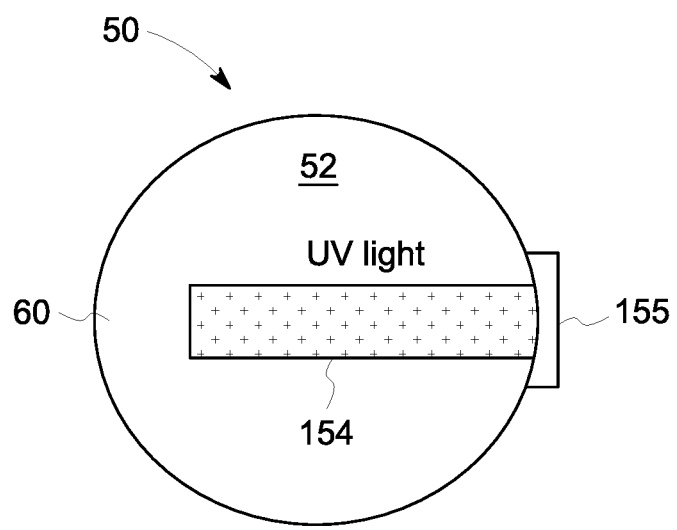

FIGS. 8A-9B depict two additional embodiments for providing sanitization of the moisture management system 40 according to the present disclosure. In the embodiment of FIGS. 8A-8B, a UV light source 154 is provided at least in part within the first reservoir 60 of the water trap 50 (which may be in addition to, or in the alternative to providing one in the evaporation chamber 70, for example). In the embodiment shown, the UV light source 154 extends into the first reservoir 60, powered by a power unit 155 positioned outside the water trap 50. The UV light source 154 is configured to irradiate the moisture 62 within the water trap 60 to kill pathogens therein, thereby preventing growth to contaminate the medical device 2 and/or to result in contaminated evaporated moisture from exiting the exhaust 78 of the evaporation chamber 70.

Figure 9A:
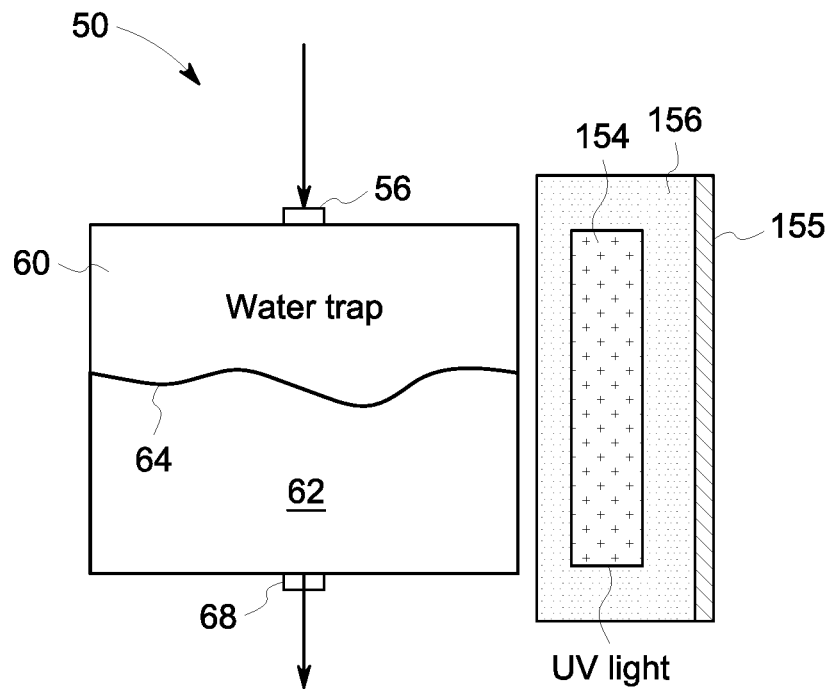
FIGS. 9A and 9B depict side and top views of another alternate embodiment of water trap as may be incorporated within the systems depicted in FIGS. 5 and 6.
Figure 9B:
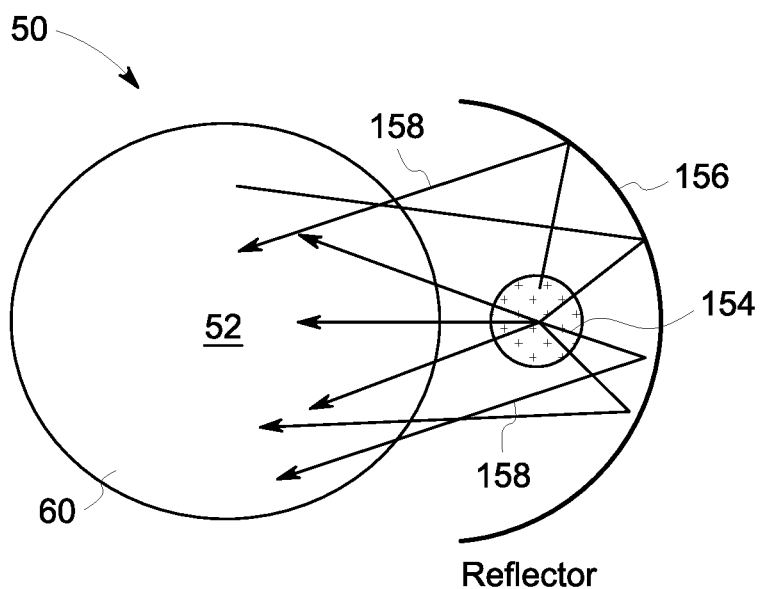

In other embodiments, such as that shown in FIGS. 9A-9B, the UV light source 154 is provided outside of the water trap 50, but positioned so as to emit UV light on the moisture 62 retained within the first reservoir 60. In this example, the water trap 50 and particularly the first reservoir 60 may be comprised of a clear or otherwise UV-emissible material, such as polycarbonate. A reflector 156 is provided on an opposite side of the UV light source 154 from the water trap 50 so as to direct the light beams 158 from the UV light source 154 into the first reservoir 60. This configuration again provides for the elimination of pathogens within the moisture 62 on the first reservoir 60, that simplifies the design by not requiring the UV light source 154 to be provided in contact with the moisture 62.

Figure 10:
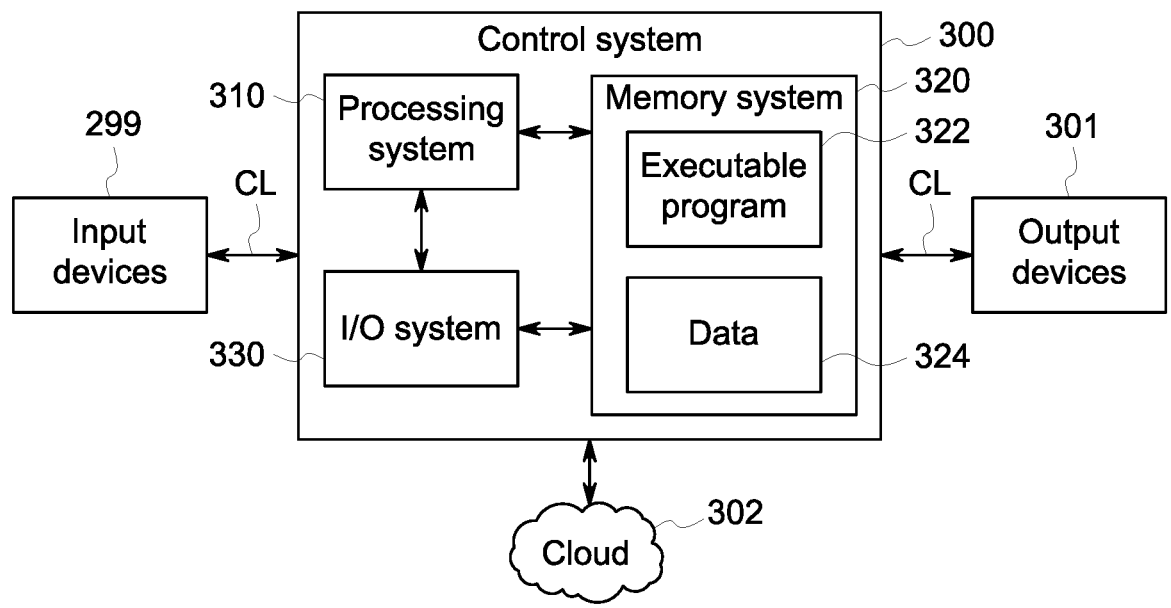
FIG. 10 is a schematic view of an exemplary control system as may be incorporated within the moisture management systems depicted in FIGS. 5 and 6.

FIG. 10 depicts an exemplary control system 300 for operating valves and/or powered devices 110 or other aspects of the moisture management systems 40 discussed above. The control system 300 may be dedicated for the moisture management system 40 (for example in the case of a retrofittable design), and/or modified versions of existing control systems that operate the medical devices 2. Certain aspects of the present disclosure are described or depicted as functional and/or logical block components or processing steps, which may be performed by any number of hardware, software, and/or firmware components configured to perform the specified functions. For example, certain embodiments employ integrated circuit components, such as memory elements, digital signal processing elements, logic elements, look-up tables, or the like, configured to carry out a variety of functions under the control of one or more processors or other control devices. The connections between functional and logical block components are merely exemplary, which may be direct or indirect, and may follow alternate pathways.

In certain examples, the control system 300 communicates with each of the one or more components of the system 40 via a communication link CL, which can be any wired or wireless link. The control module 300 is capable of receiving information and/or controlling one or more operational characteristics of the system 40 and its various sub-systems by sending and receiving control signals via the communication links CL. In one example, the communication link CL is a controller area network (CAN) bus; however, other types of links could be used. It will be recognized that the extent of connections and the communication links CL may in fact be one or more shared connections, or links, among some or all of the components in the system 40. Moreover, the communication link CL lines are meant only to demonstrate that the various control elements are capable of communicating with one another, and do not represent actual wiring connections between the various elements, nor do they represent the only paths of communication between the elements. Additionally, the system 40 may incorporate various types of communication devices and systems, and thus the illustrated communication links CL may in fact represent various different types of wireless and/or wired data communication systems.

The control system 300 may be a computing system that includes a processing system 310, memory system 320, and input/output (I/O) system 330 for communicating with other devices, such as input devices 299 (e.g., fill level sensors) and output devices 301 (e.g., powered devices 110 and/or valves), either of which may also or alternatively be stored in a cloud 302. The processing system 310 loads and executes an executable program 322 from the memory system 320, accesses data 324 stored within the memory system 320, and directs the system 40 to operate as described in further detail below.

The processing system 310 may be implemented as a single microprocessor or other circuitry, or be distributed across multiple processing devices or sub-systems that cooperate to execute the executable program 322 from the memory system 320. Non-limiting examples of the processing system include general purpose central processing units, application specific processors, and logic devices.

The memory system 320 may comprise any storage media readable by the processing system 310 and capable of storing the executable program 322 and/or data 324 (including thresholds for controlling the moisture management system, for example). The memory system 320 may be implemented as a single storage device, or be distributed across multiple storage devices or sub-systems that cooperate to store computer readable instructions, data structures, program modules, or other data. The memory system 320 may include volatile and/or non-volatile systems, and may include removable and/or non-removable media implemented in any method or technology for storage of information. The storage media may include non-transitory and/or transitory storage media, including random access memory, read only memory, magnetic discs, optical discs, flash memory, virtual memory, and non-virtual memory, magnetic storage devices, or any other medium which can be used to store information and be accessed by an instruction execution system, for example.

Accordingly, the systems and methods described above eliminate the manual draining of water traps, while also providing for the collection of moisture within the medical device 2, condensing the water back into the room to directly eliminate the risk of water on the floor and/or bacterial growth within the medical device 2. This also prevents water from getting into the breathing system, including by the embodiment of FIG. 6 in which the first and second water trap valves 146, 148 are closed and a bypass valve 144 opened during the draining process. This effectively creates a failsafe system in the event of a failure of one of the valves to the evaporation chamber 70, and/or a failure of the evaporation system 70 in general.

In certain embodiments, moisture detectors 160, 170 are also provided, as shown in FIG. 6. The moisture detectors 160, 170 may be of types presently known in the art. In this example, the moisture detector 160 serves as an indication that the incoming gas from the supply connection 8 may be outside specifications. This may provide a warning to the user (e.g, as an alarm or error message provided on the user interface device or a separate alarm) of poor quality, and/or an indication that the moisture management system 40 will likely not be able to keep up with the amount of moisture being introduced. Similarly, the moisture detector 170 may be provided between the water trap 50 and patient connection 10, here determining that the moisture management system 40 is somehow not keeping up or has a failure and that excess moisture is being delivered to the patient. The user may again be warned via the user interface device 4 or a separate alarm. In certain embodiments, the measurement from the moisture detector 170 is an input for how the moisture management system 40 will operate, for example increasing the energy provided to the powered devices 110 therein.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. Certain terms have been used for brevity, clarity, and understanding. No unnecessary limitations are to be inferred therefrom beyond the requirement of the prior art because such terms are used for descriptive purposes only and are intended to be broadly construed. The patentable scope of the invention is defined by the claims and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

What is claimed is:

1. A moisture management system for a medical device having a supply connection for receiving gas and a patient connection for supplying the gas to a patient, the system comprising:
   a water trap having a water trap inlet, an outlet, a first reservoir, and a drain, the water trap inlet receiving the gas from the supply connection and the outlet returning the gas to the patient connection, wherein the water trap is configured to remove moisture from the gas flowing from the water trap inlet to the outlet, and wherein the moisture removed is held in the first reservoir;
   an evaporation chamber having an evaporation inlet, an exhaust, and a second reservoir, wherein the evaporation inlet is fluidly coupled to the drain of the water trap to receive the moisture from the first reservoir, wherein the moisture is subsequently held in the second reservoir, and wherein the evaporation chamber is configured such that the moisture evaporates within the second reservoir and exits as vapor via the exhaust; and
   an evaporator that increases a rate at which the moisture in the second reservoir evaporates via the exhaust.

2. The system according to claim 1, wherein the evaporator is a fan that blows air across the moisture in the second reservoir to increase the rate of evaporation from the evaporation chamber.

3. The system according to claim 1, wherein the evaporator is a wick positioned to draw the moisture upwardly from the second reservoir to increase the rate of evaporation from the evaporation chamber.

4. The system according to claim 1, wherein the evaporator is a heater positioned in the second reservoir such that the heater warms the moisture therein to increase the rate of evaporation from the evaporation chamber.

5. The system according to claim 4, wherein the heater is a PTC heater.

6. The system according to claim 5, wherein the heater is configured to remain at or below 50° C.

7. The system according to claim 1, further comprising:
   a first level sensor positioned to detect when the moisture in the first reservoir exceeds a first threshold;
   a drain valve fluidly coupled between the drain of the water trap and the evaporation inlet of the evaporation chamber to control flow therebetween, wherein the drain valve is normally closed; and
   a control system coupled to the first level sensor and the drain valve, wherein the control system causes the drain valve to open while the first level sensor detects that the moisture in the first reservoir exceeds the first threshold.

8. The system according to claim 7, further comprising a bypass valve that bypasses the water trap to fluidly couple the supply connection and the patient connection, wherein the bypass valve is normally closed, and wherein the control system further causes the bypass valve to open while the first level sensor detects that the moisture in the first reservoir exceeds the first threshold.

9. The system according to claim 8, further comprising a first water trap valve fluidly coupled between the supply connection and one of the water trap inlet and the outlet of the water trap to control flow therebetween, wherein the first water trap valve is normally open, and wherein the control system further causes the first water trap valve to close while the first level sensor detects that the moisture in the first reservoir exceeds the first threshold.

10. The system according to claim 9, wherein the first water trap valve is fluidly coupled between the supply connection and the water trap inlet, further comprising a second water trap valve fluidly coupled between the outlet of the water trap and the patient connection to control flow therebetween, wherein the second water trap valve is normally open, and wherein the control system further causes the second water trap valve to close while the first level sensor detects that the moisture in the first reservoir exceeds the first threshold.

11. The system according to claim 9, wherein the evaporator is a powered device, further comprising a second level sensor positioned to detect when the moisture in the second reservoir exceeds a second threshold, wherein the control system increases the power to the evaporator while the second level sensor detects that the moisture in the second reservoir exceeds the second threshold.

12. The system according to claim 1, further comprising:
a second level sensor positioned to detect when the moisture in the second reservoir exceeds a second threshold; and
a control system coupled to the second level sensor and the evaporator, wherein the evaporator is a powered device, and wherein the control system increases the power to the evaporator while the second level sensor detects that the moisture in the second reservoir exceeds the second threshold.

13. The system according to claim 1, further comprising a UV light position to irradiate the moisture within at least one of the first reservoir and the second reservoir.

14. The system according to claim 1, wherein the supply connection supplies the gas to the patient from an anesthesia machine, and wherein the patient connection receives the gas from the patient back to the anesthesia machine.

15. The system according to claim 1, wherein the evaporation chamber is non-permeable to moisture.

16. A method for managing moisture for a medical device having a supply connection for receiving gas and a patient connection for supplying the gas to a patient, the method comprising:
fluidly coupling a water trap to the primary conduct, the water trap having a water trap inlet, an outlet, a first reservoir, and a drain, the water trap inlet receiving the gas from the supply connection and the outlet returning the gas to the patient connection, wherein the water trap is configured to remove moisture from the gas flowing from the water trap inlet to the outlet, and wherein the moisture removed is held in the first reservoir;
fluidly coupling an evaporation chamber to the drain of the water trap, the evaporation chamber having an evaporation inlet, an exhaust, and a second reservoir, wherein the evaporation inlet is fluidly coupled to the drain of the water trap to receive the moisture from the first reservoir, wherein the moisture is subsequently held in the second reservoir, and wherein the evaporation chamber is configured such that the moisture evaporates within the second reservoir and exits as vapor via the exhaust; and
positioning an evaporator in proximity to the second reservoir such that the evaporator acts on the moisture within the second reservoir to increase a rate at which the moisture evaporates therefrom via the exhaust.

17. The method according to claim 16, further comprising:
positioning a first level sensor to detect when the moisture in the first reservoir exceeds a first threshold;
fluidly coupling a drain valve between the drain of the water trap and the evaporation inlet of the evaporation chamber to control flow therebetween, wherein the drain valve is normally closed; and
coupling a control system to the first level sensor and the drain valve and configuring the control system to cause the drain valve to open while the first level sensor detects that the moisture in the first reservoir exceeds the first threshold.

18. The method according to claim 17, further comprising:
fluidly coupling a bypass valve that bypasses the water trap to fluidly couple the supply connection and the patient connection, wherein the bypass valve is normally closed;
fluidly coupling a first water trap valve between the supply connection and one of the water trap inlet and the outlet of the water trap to control flow therebetween, wherein the first water trap valve is normally open; and
configuring the control system to further cause the bypass valve to open and the first water trap valve to close while the first level sensor detects that the moisture in the first reservoir exceeds the first threshold.

19. The method according to claim 18, wherein the evaporator is a powered device, further comprising positioning a second level sensor to detect when the moisture in the second reservoir exceeds a second threshold, and further comprising configuring the control system to increase the power to the evaporator while the second level sensor detects that the moisture in the second reservoir exceeds the second threshold.

20. A moisture management system for a medical device having a supply connection for receiving gas and a patient connection for supplying the gas to a patient, the system comprising:
a water trap having a water trap inlet, an outlet, a first reservoir, and a drain, the water trap inlet being coupled via a first water trap valve to the supply connection for receiving the gas therefrom, the outlet being coupled via a second water trap valve to the patient connection for supplying the gas thereto, wherein the first and second water trap valves are normally open, wherein the water trap is configured to remove moisture from the gas flowing from the water trap inlet to the outlet, and wherein the moisture removed is held in the first reservoir;
an evaporation chamber having an evaporation inlet, an exhaust, and a second reservoir, wherein the evaporation inlet is fluidly coupled via a drain valve to the drain of the water trap to receive the moisture from the first reservoir, wherein the drain valve is normally closed, wherein the moisture is subsequently held in the second reservoir, and wherein the evaporation chamber is configured such that the moisture evaporates from the second reservoir and exits as vapor via the exhaust;
a bypass valve that bypasses the water trap to fluidly couple the supply connection and the patient connection, wherein the bypass valve is normally closed;
first and second level sensors positioned to detect when the moisture in the first and second reservoirs exceeds first and second thresholds, respectively;
a fan that blows air across the moisture in the second reservoir to increase a rate of evaporation of the moisture from the evaporation chamber;
a heater positioned in the second reservoir such that the heater warms the moisture therein to increase the rate of evaporation from the evaporation chamber; and
a control system coupled to the first and second level sensors, the bypass valve, the first and second water trap valves, and the drain valve, wherein the control system causes the bypass valve to open, the first and second water trap valves to close, and the drain valve to open while the first level sensor detects that the moisture in the first reservoir exceeds the first threshold, and wherein the control system increases the power to the evaporator while the second level sensor detects that the moisture in the second reservoir exceeds the second threshold.

\* \* \* \* \*